(12) United States Patent
Clark

(10) Patent No.: US 9,588,057 B2
(45) Date of Patent: Mar. 7, 2017

(54) METHOD AND DEVICE FOR RAPIDLY DETECTING CONTAMINANTS ON HIGH TOUCH SURFACES

(71) Applicant: Joseph T. Clark, Newtown, PA (US)

(72) Inventor: Joseph T. Clark, Newtown, PA (US)

(*) Notice: Subject to any disclaimer, the term of this patent is extended or adjusted under 35 U.S.C. 154(b) by 0 days.

(21) Appl. No.: 14/718,141

(22) Filed: May 21, 2015

(65) Prior Publication Data
US 2016/0341672 A1 Nov. 24, 2016

(51) Int. Cl.
G01N 21/03 (2006.01)
G01N 21/94 (2006.01)

(52) U.S. Cl.
CPC ....... *G01N 21/94* (2013.01); *G01N 2021/945* (2013.01)

(58) Field of Classification Search
CPC ......... A47L 13/10; A47L 13/42; G01N 21/94; G01N 21/8803; G01N 15/0612; G01N 2201/0221; G01N 2021/945
USPC ............................ 362/91, 109, 120, 155, 253
See application file for complete search history.

(56) References Cited

U.S. PATENT DOCUMENTS

| | | | |
|---|---|---|---|
| 1,621,645 A | 3/1927 | Thorp | |
| 2,599,253 A | 6/1952 | Gits et al. | |
| 3,134,129 A | 5/1964 | Allen | |
| 3,747,154 A | 7/1973 | O'Neil et al. | |
| 4,586,741 A | 5/1986 | Muti | |
| 5,171,086 A | 12/1992 | Baloochi | |
| 5,675,249 A * | 10/1997 | LaClair | G01N 1/34 250/227.17 |
| 5,970,633 A | 10/1999 | Jones et al. | |
| 6,170,959 B1 | 1/2001 | Richardson, III | |
| 7,484,859 B1 | 2/2009 | Burke | |
| 7,826,046 B1 | 11/2010 | Clark | |
| 8,707,499 B2 * | 4/2014 | Clark | A47L 13/10 15/105 |
| 2003/0131439 A1 * | 7/2003 | Wen | A47L 5/24 15/344 |
| 2006/0215391 A1 | 9/2006 | Jones et al. | |
| 2009/0059569 A1 | 3/2009 | Quattrini, Jr. | |

FOREIGN PATENT DOCUMENTS

| | | |
|---|---|---|
| CN | 201469208 | 5/2010 |
| CN | 201591529 | 9/2010 |
| JP | 2005-63742 | 3/2005 |

OTHER PUBLICATIONS drillspot.com, "Rubbermaid J736-67 Dust Mop Kit", 2 pages, Drillspot, 2011.
swiffer.com, "Swiffer Sweeper Product Information and Swiffer Sweeper Coupons", 1 page, Proctor & Gamble, 2011.
3m.com, "3M Easy Scrub Express Flat Mop System", 2 pages, 3M, 2007.
rubbermaidcommercial.com, "Rubbermaid HYGEN Quick Connect Frames", 2 pages, Rubbermaid Commercial Products, 2011.
grainger.com, "Tough Guy Floor Broom," 1 page, W.W. Grainger, Inc., 2011.

(Continued)

*Primary Examiner* — Sang Nguyen
(74) *Attorney, Agent, or Firm* — Florek & Endres PLLC

(57) ABSTRACT

A method and device for detecting and removing small particulate matter fluid and/or contaminants on high touch hard surfaces.

19 Claims, 3 Drawing Sheets

(56) References Cited

OTHER PUBLICATIONS grainger.com, "Tough Guy General Purpose Broom", 1 page, W.W. Grainger, Inc., 2011.
grainger.com, "Tough Guy Floor Squeegee", 1 page, W.W. Grainger, 2011.
rubbermaidforless.com, "Rubbermaid 6186-88 WaveBrake 44 Qt Side Press Combo", 2 pages, Jainsan, Inc., 2011.
Bissell, "CleanView II Bagless User's Guide", 16 pages, Bissell Homecare Inc., Grand Rapids, Michigan, 2008.
Oreck, "Oreck Vacuum Cleaners and Floor Machines", 2 pages, Oreck Direct, LLC, Nashville, Tennessee, 2011.
Dirt Devil, "Ultra Swivel Glide Bagless", 4 pages, Royal Appliance Manufacturing Company, 2011.
Hoover, "Platinum Collection Cyclonic Bagless Upright", 2 pages, Techtonic Floor Care Technology Limited, 2011.
cartersproducts.com, "SP21 Six Lamp Inspection Lights", Carter Products Co., Inc., Grand Rapids, MI, 1 page, 2011.
doylesystems.com, "Doyle Systems—Visual Inspection Systems and Print Inspection Systems", Doyle Systems, 3 pages, 2007.
barangle.com, "Barangle Clean", Barangle Corporations, 2 pages, 2011.
surefire.com, "Surefire G2 Nitrolon Single-Output Incandescent", Surefire LLC, 4 pages, 2013.

* cited by examiner

METHOD AND DEVICE FOR RAPIDLY DETECTING CONTAMINANTS ON HIGH TOUCH SURFACES

FIELD OF THE INVENTION

This invention relates to a method and device for rapidly detecting contaminants on a high touch surface (e.g. tabletop, countertop, desktop, etc.). More specifically, the invention relates to a method for detecting small particulate matter and/or contaminants on a high touch hard surface comprising of directing light from a light source onto a hard surface. The light source may comprise a single source or a plurality of light sources, such as an array of illumination to create a light beam. The light beam is directed or focused onto the high touch surface at an acute angle which will illuminate the contaminants on the high touch surface and thereby allow for removal of the contaminants. The present invention will allow small particulates or contaminants on the high touch surface to be visible with the "naked-eye" when the same small particles or contaminants are not visible when using conventional floor, wall, ceiling or table light sources.

BACKGROUND OF THE INVENTION

Unhygienic high touch surfaces such as countertops and tabletops are a dilemma in the house as well as at the workplace and can pose many health and safety risks. Almost all private households and public facilities such as restaurants, hospitals, cafeterias, prisons, schools, and manufacturing facilities require clean and hygienic food preparation, eating and work areas. Clean and hygienic food preparation, eating and work areas improve health and reduce safety risks.

A recent study released by the University of Arizona at Tucson, identified the kitchen as the most germ-contaminated area in the home. In fact, the University of Arizona study reported that countertops are one of five key "hot zones" or sites with the highest bacteria counts.

Cleaning is usually defined as the removal of foreign matter (e.g. soil, and organic matter) from objects or surfaces. If countertops and tabletops are not properly cleaned, bacteria, viruses and other and germs such as botulism, salmonella, shigella, listeria, campylobacter and hepatitis A, can thrive which poses a potential safety risk. Also, in order to stop infectious diseases before they happen, the Centers for Disease and Control Prevention recommends that people clean and disinfect counters and other surfaces before, during, and after preparing food (especially meat and poultry). Also, it is common knowledge that disinfectants are less effective if used when surfaces are not thoroughly cleaned first. Also, if soiled matter is allowed to bake or dry on a surface, the disinfectant process is even less effective. So it is important to properly clean countertops, tabletops and other high touch surfaces on a regular basis; however, no rapid test that provides real-time feedback currently exists to quickly verify that a proper cleaning has been performed on a high touch surface. As a result, visual inspection is the most relied upon method of inspection (e.g. if it looks clean with the naked eye, it must be clean enough). Unfortunately, the current visual inspection method is not very accurate and many high touch surfaces are left unclean. Countless contaminants are unnoticed and inadvertently left behind and could become a primary food source for bacteria and viruses.

Furthermore, attention to preventing contamination from ever happening in the first place is clearly preferable and having the necessary tools that enable one to monitor contamination is just as important. Even very small amounts of contamination can have dramatic consequences depending upon the environment. Because of this, countertop and tabletop surface cleaning is a necessity.

Cleaning is very important in controlling many issues as evidenced by the 100+ billion dollar U.S. Commercial and Residential Cleaning Market. America purchases many products and cleansing chemicals; however, one shortcoming of current methods is that no matter how much cleaning gets done, the user is never truly assured that the surface is thoroughly contaminate free. Improving the current cleaning procedures and methods used by people and cleaning services is needed.

There's currently no effective method to help with quality control when it comes to measuring particulate matter when inspecting hard high touch surfaces such as countertops and tabletops with the naked eye. There's also no current method to enhance one's ability to visually inspect a surface. Currently, people use the naked eye to aid in detecting contaminants however, unknown to the individuals, the illumination relied upon is often improperly and insufficiently directed onto the surface of interest to effectively detected and/or illuminate small contaminants on the counter/tabletops and other high touch surfaces. In in well-lit room, where lighting is typically dispersed from the ceiling and shines from above the area being inspected and cleaned is not sufficient to notice small particulate matter. The reason they cannot see small contaminants is because of reflective properties of the lighting in a particular room setting. When relying on light to see small contaminants, you need light to properly reflect off of the contaminants in order to see them. For example, when reflecting light, even if you allow a lot of light into the room, the amount of light reflected off of the contaminants is too small and cannot compete with the amount of light scattered about the entire room. And this inhibits you from seeing the dirt/dust.

Even if a bright light is directed straight "down" at a high touch surface, both the surface and the contaminants reflect the same bright light back towards the user's eyes, resulting in the in ability to identify and view many small contaminants on the high touch surface.

Prior methods used for detecting contaminants on high touch hard surfaces are not very effective. For example, the common "white glove" test only spot checks a small, trivial area directly underneath where the fingertip contacts the surface. As a result, numerous areas are never even tested because it is too cumbersome and not practical to swipe an entire surface with a "white glove." Also, often the contaminants are tiny, transparent or camouflaged (e.g. clear plastic, glass and crumbs, hair) and are hard to detect on a "white glove" inspection. Another example of a prior method used to detect contaminants on high touch hard surfaces is an adenosine triphosphate test (ATP). Unfortunately, this test swabs and provides feedback pertaining to the level of cleanliness of only the small area or surface that was directly swabbed. As a result, ATP would not be used to rapidly detect contaminants over an entire hard surface (example—inspect the entire countertop). Also, because of its reliance on natural light, ceiling lights, wall lights, table lamps, chandeliers, etc., the current visual inspection method with the "naked eye" is also not very effective for locating small particulate matter on hard surfaces. This is because the light relied upon is too diffused, not focused and not directed at an appropriate angle in order to effectively illuminate small particulates and contaminants such as dirt and dust particles. Lastly, these current methods only actually help users to identify small amounts of particulate manner (if that) and therefore do not afford users with the opportunity to take steps to properly remove most of many of the contaminants from the environment.

Removal of contaminants is the goal of all cleaning practices and is a very important step in the cleaning process. Therefore, there is a need for a method and device that can be easily used to quickly and thoroughly detect contaminants over entire areas of high touch hard surfaces and help avoid many health and safety risks caused by the contaminants. There is also a need for a method and device that can be used to enhance the naked-eye or visual assessment method of inspecting high touch hard surfaces.

The present invention overcomes these drawbacks and fills these and other needs.

SUMMARY OF THE INVENTION

It is the general object of the present invention to provide a method and device that effectively detects small particulates and contaminants on hard high-touch surfaces such as countertops, tabletops and bar tops.

It is another object of the present invention to provide a method and device that greatly improves a person's ability to see small particulate matter and visually inspect high touch hard surfaces.

It is a further object of the present invention to provide a small particulate and contaminant detecting device that is simple and easy to use that affords the user the ability to reduce cleaning time.

It is an additional object of the present invention to provide a method that is capable of detecting particulate matter that is typically camouflaged and not visible when relying on prior methods of exposure.

It is another object of the present invention to provide a method for quickly spot-checking large expanses of high touch hard surfaces such as countertops and tabletops to ensure the surface is contaminate free after cleaning as well as during the cleaning method or protocol.

DETAILED DESCRIPTION OF THE INVENTION

These and other objects of the present invention are achieved by the device of the present invention which comprises a light source and a portable platform so the beam or beams of light emitted from the light source(s) contact the hard surface being cleaned at an acute angle and in a focused and concentrated illuminated area. Although a single light source may be used it is preferred that the light source comprises a plurality, i.e., two or more lights sources. The device will also comprise a power source which will provide electric current to the light source allowing the light source to emit light. The power source may be a battery or a current provided from an electrical outlet via a power cord.

The device may further comprise a switch for controlling the flow of electricity from the power source to the light source.

One embodiment of the present invention is useful on hard, smooth and level surfaces, particularly countertops, tabletops and bar tops.

Figure 1:
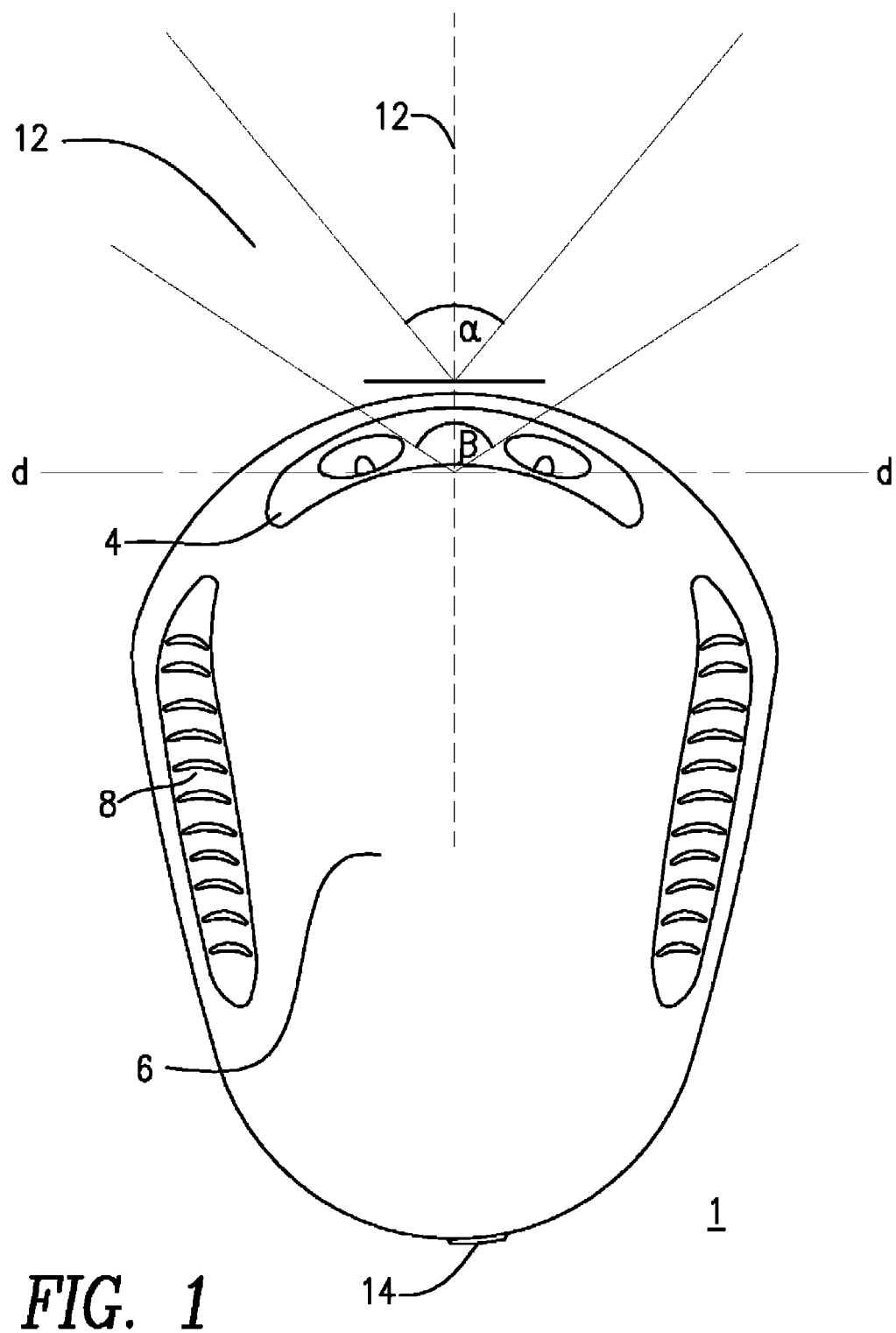
FIG. 1 is a top view of one embodiment of the present invention demonstrating the area of illumination.

It is preferred that the light source of the device provide a focused beam of light, most preferably in a single direction. Typically the light source(s) is equipped with a reflective surface that reflects and concentrates the emitted light into a single direction to create a focused and concentrated area of illumination. The focused and concentrated area of illumination is preferably an area that is 180° or less, preferably 150° or less and most preferably 130° or less when viewed from above the device and measured from the center of the device. More specifically, as shown in FIG. 1, the single direction illuminated area can be determined by drawing line d-d perpendicular to the base of the light source and determining the angle created by the edges of the illuminated area at a point about 5 inches from the center of line d-d or the center of the light source in the direction of the emitted light.

Figure 2:
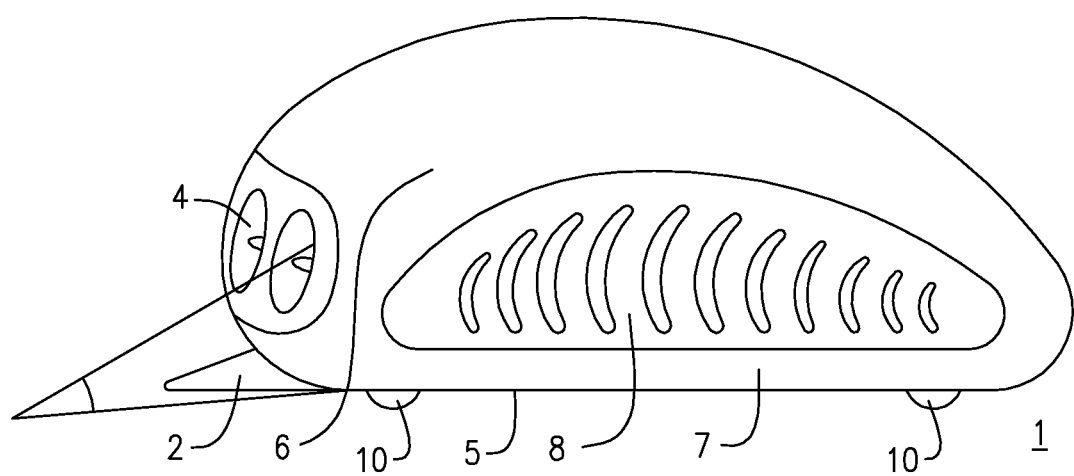
FIG. 2 is a side view of one embodiment of the present invention demonstrating the acute angle at which a light beam from the embodiment contacts the surface.

The light source should also contact the hard surface at an acute angle. As used herein the term "acute angle" means the emitted light beam for the light source should create an angle of contact with the hard surface that is less than 35° when measured from the hard surface to the base of the light source. Preferably the acute angle should be less than 30° and most preferably less than 25°. In certain embodiments, the contact angle for the emitted light source should be about 0° to about 20°, preferably about 0° to about 15° and most preferably about 0° to about 10°. More specifically, as shown in FIG. 2 the acute angle can be determined by drawing line d-d from the base of the light source to a point approximately 3 inches in front of the device. The acute angle is the angle created at the intersection of line a-a with the hard surface.

Embodiments of the light source can be a flashlight, an LED or other conventional known light sources such as an incandescent, fluorescent or high intensity discharge lamp. The following commercially available light sources were successfully tried on various embodiments of the present invention; Barangle Corporation's Barangle Clean LED, a high-intensity LED flashlight with 150 lumen output, Sure-Fire G2® Nitrolon®, a high-intensity, incandescent flashlight with 65 lumen output; SureFire G2® LED, a high-intensity, 80 lumen output flashlight, equipped with a P60L reflector assembly lamp. Based upon the testing conducted on these light sources, preferred embodiments of the present invention will employ a light source that exhibits at least 60 lumens, preferably at least 75 lumens and more preferably at least 100 lumens. In certain specific embodiments the light source will exhibit about 125 lumens or more and preferably about 150 lumens or more.

One embodiment of the device of the present invention may also include an on/off touch or motion switch or sensor for the light source which will activate or turn on the light source by the touch of the user such as the user's hand or by the movement of the device. For example the device will have an "off" mode wherein no power will be supplied to the light source and the light source will not emit light. In the "off" mode, the device may be stored or transported without power being supplied to the light source. The device will also have an "on" mode wherein power will be supplied to the light source and the light source will emit light for use of the device in detecting contaminants. In the "on" mode the power will be supplied to the light source as long as the device is in the "on" mode. The device will also have a "stand-by" mode. In the "stand-by" mode the power will be supplied to the light source for the emission of light as long as the user is touching the device or the device is moving. In the "stand-by" mode if the user is not touching the device or moving the device for a period of time, such as 5, 10 or 15 seconds, the power to the light source will be stopped and the light source will not emit light. Once the device is touched by the user or moved, the power will automatically be supplied to the light source causing the light source to emit light. The "stand-by" mode allows the conservation of power when the device is not in use. Moreover, the "stand-by" mode allows the user to quickly and easily illuminate the hard surface to check for and locate contaminants, clean the identified area without a power drain during the cleaning process and quickly and easily reactivate the power and illumination of the device to verify the cleaning of the identified contaminated area is complete and effective. The on/off switch may be a conventional electrical switch. In certain embodiments, the on/off switch will be a touch switch, i.e. contact switch that requires the user to depress and hold a portion of the device to complete the electrical connection that supplies power to the light source. In this embodiment, as soon as the user releases the pressure on the contact switch area, the electrical connection is broken and power is not supplied to the light source.

The light source is mounted, attached to or formed into the movable platform of the present invention. The movable platform can be any type of solid structure that supports the light source or sources and allows the light emitted from the light source (s) to contact the hard surface at an acute angle and in the desired illumination area.

In certain embodiments of the present invention, the movable platform is a size and shape that will easily fit in the palm of a user's hand. In this embodiment the light source(s) is formed and permanently mounted in or on the movable platform. The moveable platform further comprises a flat planar bottom surface that when in use is parallel to the hard high-touch surfaces such as countertops, tabletops and bar tops. The flat planar bottom may further comprise a structure or structures that allow the movable platform to be easily moved on the hard high-touch surface. The structure or structures that allow the movable platform to be easily moved on the hard high-touch surface may be a friction reducing component such as a teflon coating or one or more pieces of fabric such as felt that will slight raise the flat planar bottom surface of the movable platform off the hard touch surface and allow the device of the present invention to slide or glide over the hard high-touch surface. Alternatively the structure or structures that allow the movable platform to be easily moved on the hard high-touch surface may comprise wheels or roller ball(s) that will slight raise the flat planar bottom surface of the movable platform off the hard touch surface an allow the device of the present invention to slide or glide over the hard high-touch surface. The structure or structures that allow the movable platform to be easily moved on the hard high-touch surface may be any combination of the foregoing.

Some embodiments of the present invention the movable platform will comprise a top curved surface that is opposite the flat planar bottom surface of the movable platform. The top curved surface will create a convex curve when the device is viewed from the side. In certain embodiments the convex surface will extend upward from the flat planar bottom surface. Alternatively the convex surface will extend a from one or more end walls that extends upwardly, preferably in a substantially perpendicular manner, from the flat planar bottom surface before curving to create the convex surface.

Embodiments of the present invention may also comprise side walls that extend upwardly from the flat planar bottom surface, preferably in a perpendicular manner or within about ±25°, preferably within about ±20° and most preferably within about ±15° from the perpendicular 90°. The side walls will connect the flat planner bottom surface and with the top curved surface. The side walls may further comprise a structure for improving the user's hold on the device of the present invention. Examples of the structure for improving the user's hold include but are not limited to indentations on the side walls such as grooves or ridges integrally formed into the side walls. The structure for improving the user's hold may also include a high friction structure such as a rubber or foam composite adhered to the side walls. The structure for improving the user's hold may comprise a combination of any of the aforementioned structures and composites.

In certain embodiments the flat planar bottom surface, the curved top surface, the end walls if present and the side walls are formed from a hard plastic in one or more pieces.

In certain embodiments, the hard plastic used is antimicrobial.

In certain embodiments, the light source(s) is embedded or integrally formed into the top curved surface of the device and/or one of the end walls.

In certain embodiments, there may be an additional light source containing a UV light for killing microscopic contaminants.

In certain embodiments, there may be an additional light source containing a black light for detecting invisible fluorescent marker systems.

In certain embodiments of the present invention, the power source for the light source is contained within the space between the flat planar bottom surface, the top curved surface, the optional end wall and side walls.

Certain embodiments of the present invention further include a scraping structure that may be attached to the moveable platform, preferably in the front or illuminated region. The scraping structure may be formed of any rigid material such as metal, wood or plastic and may be permanently or removably attached to the movable platform, preferably the on the front portion below the light source. The scraper structure may be custom angled and sized so that it only touches the hard high-tough surface when the rear of the movable platform is lifted and front portion of the movable platform is angled downward. Thus allowing the scraper structure to scrape dried surface contaminate from the hard high-touch surface.

DETAILED DESCRIPTION OF EMBODIMENTS OF THE INVENTION

The present invention will be described in detail by reference to the following examples that are provided for illustrative purposes. The following examples should not be construed as limiting the invention. Many variations that do not depart from the spirit or scope of the present invention will suggest themselves to those skilled in the art. All such obvious modifications are within the intended scope of the invention.

EXAMPLE 1

A device 1 in accordance with the present invention is prepared as shown in FIGS. 1 and 2 which comprises at least one high intensity light beam 12 created by at least one plurality high output lamp 4 that releases a brilliant and focused light beam, preferably with at least about 100 to about 150 lumens of output, at a preset, fixed angle between α and β, preferably about 170° to about 110°. Preferably there is a plurality of lamps 4 to generate a single or uniform light beam.

The device 1 will preferably have a smooth convex top surface 6 with wheels 10 on the flat planar bottom surface 5 and side walls 7 that extend upwardly from the flat planar bottom 5 and connect the flat planar bottom 5 to the convex top surface 6. The side walls further comprise gripping pads 8, allowing users to comfortably hold device and easily guide and aim the light beam(s) 12 along any smooth hard surface.

The device 1 will also optionally comprise a scraper 2 on the front of the device 1, composed of a material from a list consisting of hard plastic, nylon, metal, ceramics, or any combination thereof. The device 1 will be portable and be able to be easily lifted by one hand allowing the user to utilize the scraper 2 to scrape hard dried or sticky contaminate from the surface using a scraping or back and forth motion.

The device 1 will also comprise a battery power source contained within the device to provide power to the light source 4 and on/off switch 14 located at the rear of the device 1 which will control the flow of power, i.e., electric current, from the battery power source to the light source 4 provides power. The device 1 may further comprise an access panel to allow the user to remove and/or replace the battery. Alternatively, the device 1 will have an access port that will allow the battery to be connected to an electrical outlet to recharge the battery at periodic intervals when needed.

The device 1 will be used by placing it on the flat surface to be cleaned or that was cleaned with the light beam(s) 12 focused on the area to be scanned for contaminants. Power is supplied to lamp or light source 4, creating the light beam 12 that will illuminate the surface at an acute angle γ, preferably about 3° to about 20°. Then the user will simply move or slide the device 1 on the surface to be cleaned or that was cleaned to scan and thereby illuminate or reveal a small particulate matter and contaminants on the surface. Once the small particulate matter and contaminants are illuminated or revealed they may be removed by conventional cleaning methods such as a cloth or sponge.

EXAMPLE 2

A device 1 similar to that described in Example 1 may be prepared wherein the wheels 10 are replaced with a plurality of felt pads which is raise the flat planar bottom surface 5 of device 1 off the flat surface to be cleaned or that was cleaned and thereby allow the device to slide over the flat surface to be cleaned or that was cleaned without scratching the flat surface to be cleaned or that was cleaned.

EXAMPLE 3

Figure 3:
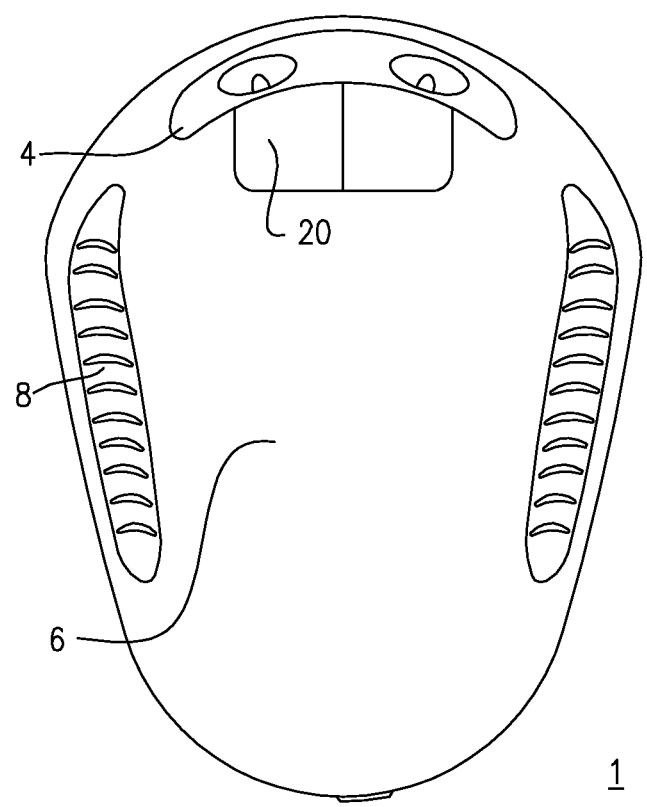
FIG. 3 is a top view of one embodiment of the present invention.

A device 1 similar to that described in Example 1 may be prepared wherein the on/off switch 14 is replaced with a contact switch the requires the user to apply pressure to a region of the device to complete the electrical connection allowing power to flow from the battery power source to the light source. When the user removes the pressure the electrical connection is broken. The contact switch may be incorporated into the either or both of the side walls 7, the gripping pads 8 or on by one or more depressible regions 20 on the front of the device as shown in FIG. 3. The device 1 may comprise two depressible regions 20 to allow easy by users that are either left or right handed.

EXAMPLE 4

A device 1 similar to that described in Example 1 may be prepared wherein the on/off switch 14 is replaced with a switch with a stand-by mode and a touch sensor which will allow power to be supplied to from the battery power source to the light source 4 when the user is touching the device 1. When the user is not touching or contacting the device 1, the electrical connection from the battery power source will be broken and the light source 4 will not be illuminated.

EXAMPLE 5

A device 1 similar to that described in Example 4 may be prepared wherein the on/off switch 14 is replaced with a switch with a stand-by mode and a motion sensor which will allow power to be supplied to from the battery power source to the light source 4 when the device 1 is moved. When the device 1 is not moving, the electrical connection from the battery power source will be broken and the light source 4 will not be illuminated. This embodiment may further comprise a timer that will break the electrical connection from the battery power source to the light source 4 after a when the device is not moved for predetermined period of time such as 15, 30, 45 or 60 seconds.

The invention illustratively described herein suitably may be practiced in the absence of any element or elements, limitation or limitations which is not specifically disclosed herein. Thus, for example, in each instance herein, any of the terms "comprising," "consisting essentially of" and "consisting of" may be replaced with either of the other two terms. The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the claims.

I claim:

1. A device used to detect small particulates, fluids or contaminants on hard high touch surfaces, comprising:
   i) one or more light sources;
   ii) a movable platform having a flat planar bottom surface that is parallel to the hard high touch surface when in use, a top surface, and side walls;
   iii) a power source for providing power to the light course;
   iv) a switch for controlling power to the light source; and
   v) a structure to assist in movement of the movable platform, selected from the group consisting of wheels, roller ball, low friction material, cloth and combinations thereof, and
wherein the light source is attached to the movable platform so that one or more light beam(s) are emitted from the device and contacts the hard surface at an acute angle of less than 35, and provides a focused and concentrated area of illumination of an area that is 150° or less, and wherein the movable platform is of a size and shape to fit into the palm of a user's hand.

2. The device as defined in claim 1 wherein each flashlight is capable of emitting a focused light beam of between about 60 and about 150 lumens.

3. A method for detecting small particulate matter or contaminants on hard high touch surfaces comprising:
 i) placing the device as described in claim 1 on a hard high touch surface;
 ii) activating the light source; and
 iii) viewing the small particulate matter or contaminants on hard high touch surface.

4. The method of claim 3 further comprising the step of
 iv) removing the viewed small particulate matter or contaminants on hard high touch surface.

5. The method of claim 4 further comprising the step of repeating steps (i) and (ii) to verify that the small particulate matter or contaminants on hard high touch surfaces were removed by step iv.

6. The device as defined in claim 1, wherein the focused and concentrated area of illumination is an area that is 130° or less.

7. The device as defined in claim 1, further comprising an additional light source that is a UV light.

8. The device as defined in claim 1, further comprising an additional light source that is a black light.

9. The device as defined in claim 1, further comprising a scraping structure that is attached to the moveable platform.

10. The device as defined in claim 1 wherein the switch is a motion switch.

11. The device as defined in claim 1 wherein the switch is a touch switch.

12. The device as defined in claim 11, wherein the touch switch is a pressure switch that requires the user to depress and hold a portion of the device to complete the electrical connection that supplies power to the light source.

13. The device as defined in claim 11, wherein the touch switch is activated by the touch of the user such as the user's hand.

14. A device used to detect small particulates, fluids or contaminants on hard high touch surfaces, comprising:
 i) one or more light sources;
 ii) a movable platform having a flat planar bottom surface that is parallel to the hard high touch surface when in use, a curved top surface, and side walls;
 iii) a power source for providing power to the light course;
 iv) a switch for controlling power to the light source; and
 v) a structure to assist in movement of the movable platform, selected from the group consisting of wheels, roller ball, low friction material, cloth and combinations thereof, and wherein the light source is attached to the movable platform so that one or more light beam(s) are emitted from the device and contacts the hard surface at an acute angle of less than 35, and provides a focused and concentrated area of illumination of an area that is 130° or less, and wherein the moveable platform is of a size and shape to fit into the palm of a user's hand.

15. The device as defined in claim 14 wherein the switch is a motion switch.

16. The device as defined in claim 14 wherein the switch is a touch switch selected from the group consisting of a touch switch that is activated by the touch of the user such as the user's hand, and a pressure switch that requires the user to depress and hold a portion of the device to complete the electrical connection that supplies power to the light source.

17. The device as defined in claim 14, further comprising an additional light source that is a UV light.

18. The device as defined in claim 14, further comprising an additional light source that is a black light.

19. The device as defined in claim 14, further comprising a scraping structure that is attached to the moveable platform.

* * * * *